US00PP24219P3

(12) United States Plant Patent
Olesen

(10) Patent No.: US PP24,219 P3
(45) Date of Patent: Feb. 11, 2014

(54) CLIMBING ROSE PLANT NAMED 'POULCY024'

(50) Latin Name: ***Rosa* hybrid**
Varietal Denomination: Poulcy024

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 42 days.

(21) Appl. No.: 13/507,033

(22) Filed: May 31, 2012

(65) Prior Publication Data

US 2013/0326742 P1 Dec. 5, 2013

(51) Int. Cl.
*A01H 5/00* (2006.01)

(52) U.S. Cl.
USPC ..... Plt./111

(58) Field of Classification Search
USPC ..... Plt./111
See application file for complete search history.

*Primary Examiner* — Kent L Bell

(57) ABSTRACT

A new garden rose plant of the Climbing class which has abundant, yellow flowers and attractive foliage. This new and distinct variety has shown to be uniform and stable in the resulting generations from asexual propagation.

1 Drawing Sheet

Botanical designation: *Rosa* hybrid.
Variety denomination: 'Poulcy024'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulcy024', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance; and
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy024' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulcy024' was selected in the spring of 2005 by the inventor as a single plant from the progeny of the aforementioned hybridization.

Asexual reproduction of 'Poulcy024' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulcy024' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcy024'. Specifically illustrated in the drawing are flowers at various stages of development, flower in parts, leaves, and stems.

DETAILED DESCRIPTION OF THE VARIETY

The following is a description of 'Poulcy024', as observed in its growth in a field nursery in Bakersfield, Calif. Observed plants are 2 years of age, and were grown on their own roots. Color references are made using The Royal Horticultural Society (London, England) Colour Chart, 2001, except where common terms of color are used.

Several physical characteristics of a non-patented rose variety 'Poulhult' are compared to 'Poulcy024' in Chart 1.

CHART 1

| | 'Poulcy024' | 'Poulhult'' |
|---|---|---|
| Petal Count | 45 | 18 to 20 |
| Flower Diameter | 50 to 80 mm | 55 to 60 |
| General Tonality of Flower Color | Yellow Group 11D with intonations of Yellow-Orange Group 16D. | Yellow-Orange 14C |

Flower and Flower Bud

Blooming habit: Continuous.
Flower bud:

*Size.*—Upon opening, 25 mm in length from base of receptacle to end of bud. Bud diameter is 13 mm.

*Bud form.*—Ovoid.

*Bud color.*—As sepals divide petals are Orange-Red Group 31B blended with Orange Group 24B.

*Sepal inner surface.*—Color: Green Group 138A. Surface: Smooth.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—22 mm long by 5 mm wide.

*Receptacle.*—Texture: Smooth. Size: 7 mm in height by 6 mm wide. Color: Yellow-Green Group 144A. Shape: Campanulate.

*Pedicel.*—Surface: Smooth. Length: About 30 mm. Diameter: 2 mm on average. Color: Yellow-Green Group 144A. Strength: Moderate.

Flower bud development: Flower buds are borne in clusters of 3 to 5 flower buds per stem. Reduced apical dominance in flower habit causes flower buds to develop evenly from the base of the plant to the upper branches.

Flower bloom:

*Fragrance.*—Moderate Chardonnay scent.

*Duration.*—The blooms have a duration on the plant of approximately 14 days. Petals fall cleanly away from plant after flowers have fully matured.

*Size.*—Flower diameter is 50 to 80 mm when open. Flower depth is 28 mm.

*Flower shape.*—General shape is initially similar to a hybrid tea, with a high tightly closed center. After the flowers open, they become cup shaped with petals that curve out from the center.

*Shape of flower, side view.*—The upper portion is a flattened convex. The lower portion is a flattened convex.

Petalage: Under normal conditions, flowers have 45 petals total, 5 to 7 of which are petaloids.

General tonality of flower: Open flowers are Yellow Group 11D with intonations of Yellow-Orange Group 16D. Tonality changes to Yellow Group 9D with intonations of Yellow Group 12B as the flower ages.

Petal color:

*Upon opening, outer and inner petals.*—Upper surface: Yellow Group 8C with intonations of Yellow Group 12A at the basal zone. Lower surface: Yellow-Orange Group 16D with intonations of Yellow-Orange Group 16B at the basal zone.

*After opening, outer and inner petals.*—Upper surface: Yellow Group 8D with Yellow Group 8A at the middle and basal zone. Lower surface: Yellow-Orange Group 14D with intonations of 14C at the middle and basal zone.

Petals:

*Petal reflex.*—Strong reflex.

*Margin.*—Entire and uniform with a point at mid apex. No undulations of margin observed.

*Shape.*—Generally narrow elliptic. Apex shape: Rounded, cuspidate. Base shape: Acute.

*Size.*—30 mm (l)×30 mm (w).

*Texture.*—Smooth.

*Thickness.*—Average.

Petaloids:

*Size.*—15 mm (l) by 7 mm (w).

*Quantity.*—Normally 5 to 7.

*Shape.*—Apex is rounded, base is acute.

*Color.*—Upper surface is Yellow Group 8D with Yellow Group 8A at the middle and basal zone. Lower surface is Yellow-Orange Group 14D with intonations of 14C at the middle and basal zone.

Reproductive organs:

*Pollen.*—None observed.

*Anthers.*—Size: 2 mm in length. Color: Yellow-Orange Group 15B. Quantity: 45 on average.

*Filaments.*—Color: Yellow-Orange Group 14A. Length: 5 mm.

*Pistils.*—Length: 5 mm. Quantity: 35 on average.

*Stigmas.*—Color: Greyed-Yellow Group 160B.

*Styles.*—Color: Red Group 41B.

*Location of stigmas.*—Level in location relative to the length of the filaments and the height of the anthers.

*Hips.*—None Observed.

Plant

Plant growth: Arching. Plants are 100 cm in height, and 100 cm wide.

Stems:

*Color.*—Juvenile growth: Yellow-Green Group 146B with light anthocyanin Greyed-Orange Group 172A. Mature growth: Yellow-Green Group 144B.

*Length.*—On average, canes are 30 cm from the base of the plant to the flowering portion.

*Diameter.*—5 mm.

*Internodes.*—On mature canes, there is an average distance of 55 mm between nodes.

*Surface texture.*—Young wood: Smooth. Older wood: Smooth.

Long prickles:

*Incidence.*—8 prickles per 10 cm of stem.

*Size.*—Average length of prickles on mature stems is 10 mm.

*Shape.*—Upper portion is linear. Lower portion is concave.

*Color.*—Juvenile prickles: Greyed-Red Group 181A. Mature prickles: Greyed-Yellow Group 160A.

Plant foliage:

*Compound leaf.*—140 mm (l)×90 mm (w).

*Quantity.*—2 leaves per 10 cm of stem on average.

*Leaf bearing angle to the stem.*—60 degrees.

*Color of juvenile foliage.*—Upper side: Yellow-Green Group 146A. Lower side: Greyed-Orange Group 166A.

*Color of mature foliage.*—Upper side: Yellow-Green Group 147A. Lower side: Yellow-Green Group 147B.

Plant leaves and leaflets:

*Stipules.*—Size: 10 mm in length. Quantity: 2 per compound leaf. Shape: Linear, slightly broad based with outward extending apices. Margins: Finely serrated. Color: Yellow-Green Group 144A.

*Petiole.*—Length: 20 mm. Diameter: 2 mm.

*Upper surface.*—Color: Yellow-Green Group 144A.

*Lower surface.*—Color: Yellow-Green Group 144B.

*Rachis.*—Length: 70 mm. Upper surface: Color: Yellow-Green Group 144A.

*Lower surface.*—Color: Yellow-Green Group 144B.

*Leaflet.*—Quantity: Normal number of leaflets per leaf in middle of the stem is 7 leaflets. Margins: Serrated. Size: Average size of the terminal leaflet on normal leaves is 53 mm in length by 38 mm wide. Shape: Generally ovate. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Climbing rose class named 'Poulcy024', substantially as illustrated and described herein, due to its abundant yellow flowers, disease resistance, and extended period of bloom.

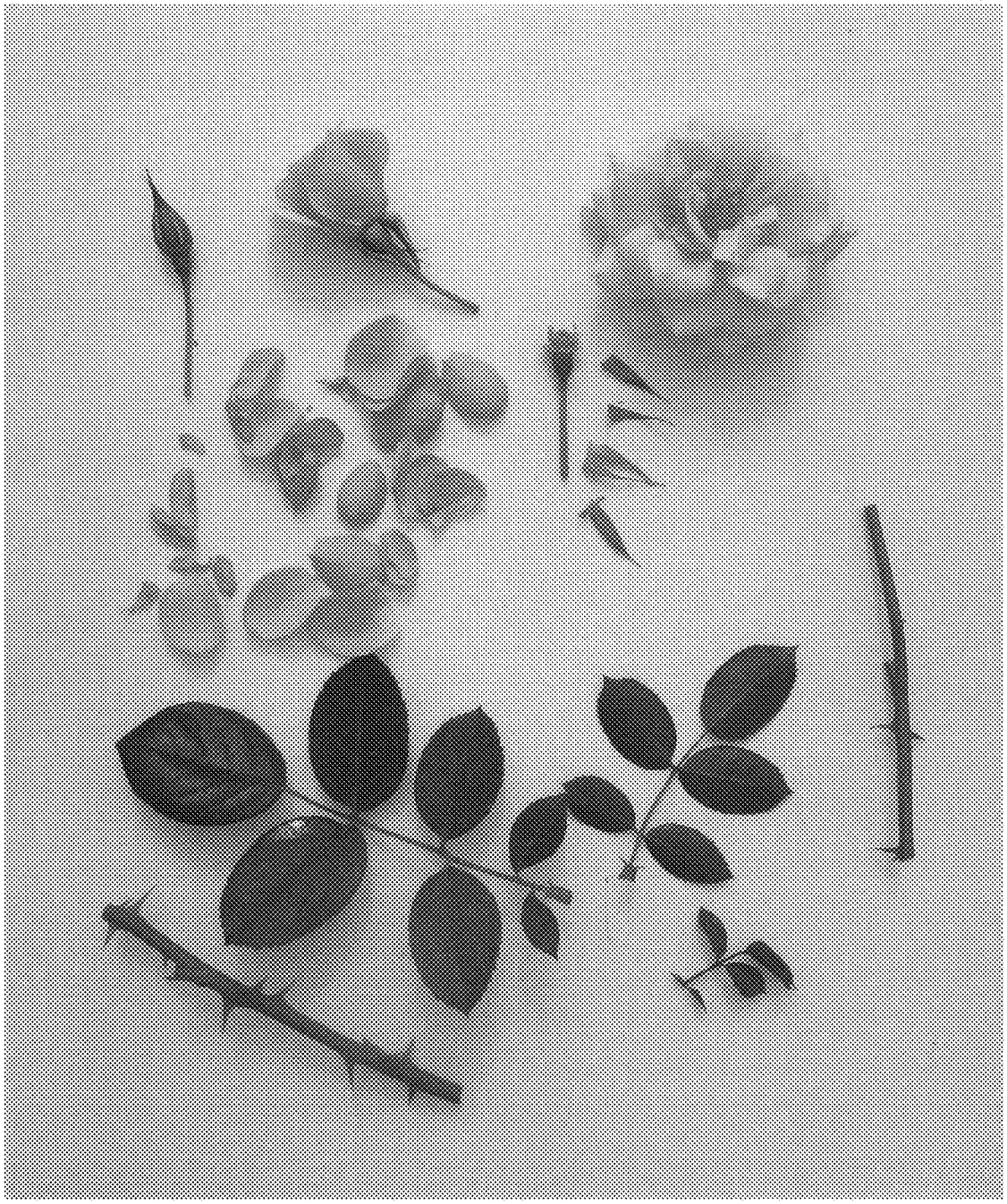

* * * * *